United States Patent [19]

Spielvogel et al.

[11] Patent Number: 5,023,513

[45] Date of Patent: Jun. 11, 1991

[54] AMINE-ALKYLBORANE DERIVATIVES AND METHODS

[75] Inventors: Bernard F. Spielvogel, Raleigh; Anup Sood, Durham, both of N.C.

[73] Assignee: Boron Biologicals, Inc., Raleigh, N.C.

[21] Appl. No.: 364,650

[22] Filed: Jun. 9, 1989

[51] Int. Cl.$^5$ .......................... A61K 31/69; C07F 5/02
[52] U.S. Cl. .......................................... 514/64; 564/9; 546/13
[58] Field of Search ................. 514/64; 546/13; 564/9

[56] References Cited

U.S. PATENT DOCUMENTS

| | | | |
|---|---|---|---|
| 4,312,989 | 1/1982 | Spielvogel et al. | 546/13 |
| 4,368,194 | 1/1983 | Spielvogel et al. | 514/64 |
| 4,587,359 | 5/1986 | Spielvogel et al. | 564/9 |

FOREIGN PATENT DOCUMENTS 0034238  4/1985  European Pat. Off. ................. 564/9

OTHER PUBLICATIONS

Publication by Spielvogel, et al., in the Journal of American Chemical Science, vol. 98, 1976, pp. 5702–5703.
Publication by Spielvogel, et al., in the Journal of American Chemical Science, vol. 102, 1980, pp. 6343–6344.
Publication by Spielvogel, et al., in Inorganic Chemistry, vol. 23, 1976, pp. 1776–1777.
Publication by Spielvogel, et al., in Inorganic Chemistry, vol. 23, 1984, pp. 4233–4324.
Publication by Spielvogel, et al., in the Journal of Pharmaceutical Sciences, vol. 70, No. 3, Mar. 1981, pp. 339–341.
Publication by Spielvogel, et al., in the Journal of Pharmaceutical Sciences, vol. 76, No. 5, May 1987, pp. 359–365.

*Primary Examiner*—Robert T. Bond
*Attorney, Agent, or Firm*—Richard E. Jenkins

[57] ABSTRACT

Novel amine-alkylborane derivatives are disclosed which exhibit significant antineoplastic and antihyperlipidemic activities. Methods for preparing the compounds are disclosed as well as methods for utilizing the compounds to induce antineoplastic and antihyperlipidemic activity.

12 Claims, No Drawings

AMINE-ALKYLBORANE DERIVATIVES AND METHODS

GOVERNMENT INTEREST

This invention may be used by the United States Government for Governmental purposes without the payment of royalty to the inventors.

DESCRIPTION

1. Technical Field

This invention relates to boron-containing compounds. More specifically, the present invention relates to novel amine-alkylborane derivatives which exhibit antineoplastic and antihyperlipidemic activity. The present invention also relates to methods for preparing and utilizing the novel amine-alkylborane derivatives.

2. Background Art

Various boron-containing compounds have previously been shown to exhibit therapeutic biological activity. For example, amine borane compounds such as $(CH_3)_3N \cdot BH_2COOH$ and $R_1R_2NB \cdot BH_2C(O)NHR_3$ have been shown to exhibit antitumor and antihyperlipidemic activities as discussed in U.S. Pat. No. 4,587,359. Additionally, various boron dipeptide compounds which exhibit antineoplastic and antihyperlipidemic activity are disclosed in copending U.S. patent application Ser. No. 179,555, filed Apr. 8, 1988, now U.S. Pat. No. 4,977,268.

All boron-containing compounds which have previously been shown to exhibit therapeutic activity have been limited to compounds related to the boron analogs of the simple amino acid glycine. In other words, all previous compounds contained boron in the form of a —$NBH_2R$—fragment. Boron-containing compounds not limited to the —$NBH_2R$—fragment are needed in order to increase the arsenal of boron compounds used for therapeutic purposes and to broaden the application of those compounds to cover therapeutic activities which may be specific for boron analogs of higher amino acids such as alanine.

DISCLOSURE OF THE INVENTION

The boron compounds of the present invention are not based on the amino acid glycine and therefore represent a significant advancement over the types of boron compounds and corresponding therapeutic activities presently available. The compounds of the present invention have been shown to exhibit significant antineoplastic and antihyperlipidemic activity. The present amine-alkylborane derivatives correspond to the general formula:

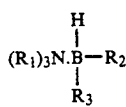

wherein $R_1$ is simultaneously or independently H, $CH_3$, or $CH_2CH_3$ with the proviso that when $(R_1)_3N$ is a primary amine, the alkyl $R_1$ can be $C_1$–$C_{10}$ linear alkyl. $R_2$ is $C_1$–$C_{10}$ alkyl or corresponds to the R group of the common amino acids. $R_3$ is I, CN, $CNCH_2CH_3+BF_4$—or $C(O)N(H)CH_2CH_3$.

Another aspect of the present invention relates to processes for preparing the amine-alkylborane derivatives disclosed herein. It has been discovered that the present amine-alkylborane derivatives can be prepared from certain alkylborane compounds through a novel multistep process. Both the intermediate products and the final product of this multistep process constitute the amine-alkylborane derivatives of the present invention.

It is therefore an object of the present invention to provide new amine-alkylborane derivatives which are active antineoplastic and antihyperlipidemic agents.

It is another object of the present invention to provide new processes for synthesizing amine-alkylborane derivatives which exhibit antineoplastic and antihyperlipidemic activity.

BEST MODE FOR CARRYING OUT THE INVENTION

The novel amine-alkylborane derivatives of the present invention contain the —$NBHRR'$—fragment as compared to the —$NBH_2R$—fragment contained in prior boron-containing compounds. The amine-alkylborane derivatives of the present invention correspond to the following general formula:

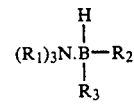

wherein $R_1$ is simultaneously or independently H, $CH_3$, or $CH_2CH_3$ with the proviso that when $(R_1)_3N$ is a primary amine, the alkyl $R_1$ can be $C_1$–$C_{10}$ linear alkyl. $R_2$ is $C_1$–$C_{10}$ alkyl or corresponds to the R group of the common amino acids and $R_3$ is I, CN, $CNCH_2CH_3+BF_4$—or $C(O)N(H)CH_2CH_3$.

The R group of the common amino acids herein refers to the R group which varies from one common amino acid to another but not including H for glycine. For example, R=$CH_3$ for alanine and R=$CH(CH_3)_2$ for valine. The common amino acids and their corresponding R group structures are well known and include alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine and histidine.

$R_1$ is preferably H, $R_2$ is preferably $C_1$–$C_5$ alkyl and $R_3$ is preferably $C(O)N(H)CH_2CH_3$.

The amine-alkylborane derivatives of the present invention have been shown to exhibit significant antineoplastic and antihyperlipidemic activity. For example, trimethylamine-methylcyanoborane ($R_1$, $R_2$=$CH_3$, $R_3$=CN) and trimethylamine-(N-ethylcarbamoyl)methylborane ($R_1$, $R_2$=$CH_3$, $R_3$=$C(O)N(H)CH_2CH_3$) demonstrated 84% and 88% inhibition, respectively, when tested at a dose of 20 mg/kg in the well known Ehrlich ascites carcinoma tumor screen with $CF_1$ male mice. The trimethylamine-methylcyanoborane and trimethylamine-(N-ethylcarbamoyl)methylborane compounds also lowered cholesterol levels 30% and 18%, respectively, after dosing for 15 days at 8 mg/kg (ip) and lowered triglycerides levels of 4% and 33%, respectively, after 9 days at a dose of 8 mg/kg per day in $CF_1$ male mice.

The multistep process of the present invention utilizes certain boron-containing compounds as the starting material to eventually produce an amine-(N-alkylcarbamoyl)alkylborane as the final product. The starting amine-alkylboranes can be prepared by methods known in the art such as described in M. F. Hawthorne *J. Amer.*

Chem. Soc. 83:831 (1961). The present process comprises five basic steps which are shown in the following schematic representation:

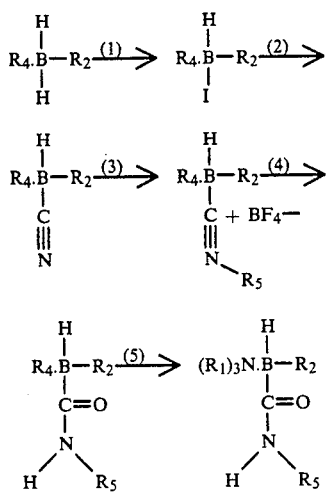

In the above scheme, $R_4$ represents an amine of the starting amine-alkylborane compound and $R_4$ can be any primary, secondary, tertiary or heterocyclic amine. The alkyl groups of any primary, secondary or tertiary $R_4$ amine can independently or simultaneously be $C_1$-$C_{10}$ alkyl and the carbon ring of any heterocyclic $R_4$ amine can range from 4 to 10 carbon atoms. The starting compound is preferably a trialkylamine-alkylborane and is most preferably trimethylamine-alkylborane. $R_1$ and $R_2$ are as defined hereinbefore.

The process initially involves treating the aminealkylborane with iodine in the presence of benzene to produce the iodo-substituted product which is then reacted with cyanide ion in the presence of a solvent to substitute cyanide for the iodine. The cyanide ion can be used in any form such as NaCN, KCN, or LiCN and is preferably utilized as NaCN. The solvent can be any ether solvent such as diethyl ether and is preferably tetrahydrofuran (THF). The cyano-substituted product is then alkylated with the alkylating agent $(R_5)_3OBF_4$ wherein $R_5$ is methyl, ethyl or propyl, and is preferably ethyl. The alkylating agent is utilized with a solvent such as dichloromethane or chloroform. The alkylated cyano group is then converted to an amide by hydroxide ion in the form of, for example, NaOH, KOH, LiOH, $Mg(OH)_2$ or $Ca(OH)_2$. The original amine group of the starting amine-alkylborane is then replaced by a second amine by reacting the amide product with an amine of the formula $(R_1)_3N$ wherein $R_1$ is as defined hereinbefore.

It should be noted that the above process comprises individual reaction steps which can individually be utilized to prepare the full range of amine-alkyborane derivatives of the present invention.

It has also been discovered that the starting material amine-methylborane can be produced by a convenient process not heretofore known in the art. This process is shown in the following schematic representation:

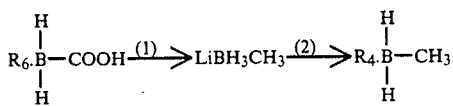

In the above amine-carboxyborane, $R_6$ represents the same generic amine as $R_4$ and $R_4$ and $R_6$ can be the same or different. The process utilizes an amine-carboxyborane which can be prepared by methods known in the art such as described in Spielvogel et al. J. Amer. Chem. Soc. 98:5702 (1976). The amine-carboxyborane is first reacted with $LiAlH_4$ to form $LiBH_3CH_3$ which is then treated with $R_4$ HCl wherein $R_4$ is as defined hereinbefore to create the amine-methylborane.

The amine-alkylborane derivatives prepared by the processes of the present invention can be administered to an animal in therapeutically effective amounts utilizing well known administration techniques and carriers. Therapeutically effective amount herein refers to an amount sufficient to bring about a desired level of pharmaceutical activity. Due to the unknown toxic effect of boron compounds, actual human tests have not been conducted. Nevertheless, the present invention fully contemplates the use of the present boron compounds on human subjects in order to treat cancer and control serum lipid levels and animal as used herein is intended to include humans.

SPECIFIC EMBODIMENTS

The following examples are included for the purpose of illustration only and are not to be construed to limit the scope of the invention or claims. Unless otherwise indicated, all parts and percentages are by weight.

EXAMPLE 1

Trimethylamine-methylborane

To a suspension of trimethylamine-carboxyborane (15.00 g, 128.25 mmol) in anhydrous diethyl ether (300 ml) at room temperature under $N_2$ was slowly added with stirring a solution of lithium aluminum hydride (256 ml of 1 M solution is diethyl ether). After complete addition, the mixture was heated at reflux for 3.5 h. It was cooled to 0° C. and trimethylamine hydrochloride (50.00 g, 523.18 mmol) was added in several batches (3-4 g each time). The mixture was stirred at 0° C. for 0.75 h. $^{11}B$ nmr of a small aliquot showed complete conversion to trimethylamine-methylborane. The excess lithium aluminum hydride was still reacting with trimethylamine hydrochloride so the mixture was allowed to stir at room temperature overnight. To this more trimethylamine hydrochloride (22.5 g, 238.05 mmol) was added and the mixture was stirred for another 2 h. It was then slowly poured onto a mixture of ice water and diethyl ether (ca 3:1, 800 ml). The inorganic solids were filtered and washed with diethyl ether (2×100 ml). The organic layer was separated from the filtrate and the aqueous layer was extracted with diethyl ether (2×350 ml). The combined organic portions were dried over anhydrous magnesium sulfate, concentrated on rotary evaporator at room temperature, redried on small amount of anhydrous sodium sulfate and the solvent was removed at room temperature. The residue was kept in vacuo for 1 minute. Yield 7.67 g, 68.77%.

EXAMPLE 2

Trimethylamine-methylcyanoborane

To a solution of trimethylamine-methylborane (6.80 g, 78.19 mmol) in anhydrous benzene (80 ml) at 0° C. under $N_2$ was slowly added solid iodine (8.50 g, 33.49 mmol) over a period of 40 minutes. After complete addition, the pinkish white solution was allowed to warm and stirred at room temperature for 1 h. The solvent was removed under reduced pressure and the residue was kept in vacuo in the dark overnight. The pinkish white solid (14.38 g) was taken with sodium cyanide (7.7 g, 97.46 mmol) in anhydrous tetrahydrofuran (140 ml) under $N_2$. After initial vigorous reaction, the mixture was heated at reflux for 2.5 days. The mixture was cooled to room temperature, filtered and the residue was washed with tetrahydrofuran (2×15 ml). The combined filtrate was concentrated under reduced pressure. The residue was taken in dichloromethane (ca 75 ml), washed with water (3 ×75 ml), dried over anhydrous sodium sulfate and the solvent was removed under reduced pressure to give a mixture of clear oil and white solid. It was purified by flash chromatography on silica gel. The column was first eluted with diethyl ether:hexane (8:2) and after collecting 60 fractions of ca 35–40 ml each, it was eluted with dichloromethane (200 ml) followed by methanol (250 ml). The product eluted with diethyl ether: hexane in fractions 19–45. A side product, trimethylamine-methyldicyanoborane eluted with dichloromethane and methanol. Trimethylamine-methylcyanoborane: White hygroscopic semisolid, yield 1.75 g, 19.99% (23.33% based on iodine). Trimethylamine-methyldicyanoborane: White solid, mp 193° –197° C. Yield 0.57 g, 5.32%.

EXAMPLE 3

Trimethylamine-(N-ethylcarbamoyl)methylborane

Trimethylamine-methylcyanoborane (0.71 g, 4.20 mmol) in anhydrous dichloromethane (2.0 ml) was taken with a solution of triethyloxonium tetrafluoroborate (3.8 ml of 2.22 M solution in dichloromethane), under a static atmosphere of nitrogen. The mixture was stirred at room temperature for 24 h. It was cooled to 0° C., slowly brought to pH=11 by addition of 1 N NaOH and stirred at 0° C. After ca 0.25 h, it was diluted with dichloromethane (ca 15 ml) and 1 N NaOH (ca 20 ml) and stirred at room temperature for 2 days. The organic layer was separated and the aqueous layer was extracted with dichloromethane (2×35 ml). The organic extracts were combined, dried over anhydrous sodium sulfate and the solvent was removed under reduced pressure to give an oil. The product was purified by dry flash chromatography on silica gel using dichloromethane (4×25 ml), followed by dichloro-methane:acetone (8:2, 4×25 ml) and finally dichloromethane:methanol (8:2, 10×35 ml). The product was obtained as a clear colorless oil from dichloro-methane:methanol fractions. Yield 0.58 g, 87.37%. The product could also be purified by normal flash chromatography on silica gell using diethylether:dichloromethane (9:1, 500 ml) followed by dichloromethane-methanol (8:2, 500 ml) with similar yield.

EXAMPLE 4

Ammonia-(N-ethylcarbamoyl)methylborane

Ammonia (ca 45 ml) was condensed at −78° C. and transferred to a precooled stainless steel pressure reaction vessel containing trimethylamine-N-ethylcarbamoyl methylborane (0.42 g). The vessel was closed, allowed to warm to room temperature and then heated at 58–60° C. After ca 14 h, it was cooled to −78° C., opened, allowed to warm to room temperature and the ammonia was allowed to escape into the atmosphere. The residue was taken in diethyl ether, filtered and the solvent was removed under reduced pressure to given an oil (0.20 g). The product was purified by dry flash chromatography on silica gel using ethyl acetate (4×30 ml), followed by ethyl acetate:methanol (49:1); 8×30 ml) and finally ethyl acetate:methanol (19:1, 15×30 ml). The product was obtained from ethyl acetate:methanol (19:1) fractions, as a white solid: mp. 90–92° C. Yield 0.14 g, 45.43%.

It will be understood that various details of the invention may be changed without departing from the scope of the invention. Furthermore, the foregoing description is for the purpose of illustration only, and not for the purpose of limitation—the invention being defined by the following claims.

What is claimed is:

1. An amine-alkylborane derivative corresponding to the general formula:

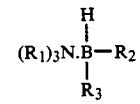

wherein $R_1$ is simultaneously or independently H, $CH_3$, or $CH_2CH_3$, with the proviso that when $(R_1)_3N$ is a primary amine, the alkyl $R_1$ can be $C_1$-$C_{10}$ linear alkyl; $R_2$ is $C_1$-$C_{10}$ alkyl or corresponds to the R group of the common amino acids; and $R_3$ is I, CN, $CNCH_2CH_3+BF_4-$ or $C(O)N(H)CH_2CH_3$.

2. An amine-alkylborane derivative according to claim 1 wherein $R_1$ and $R_2$ are $CH_3$ and $R_3$ is selected from the group consisting of I, CN, and $CNCH_2CH_3+BF_4-$.

3. An amine-alkylborane derivative according to claim 1 wherein $R_1$ is H, $R_2$ is $CH_3$ and $R_3$ is $C(O)N(H)CH_2CH_3$.

4. A process for the preparation of amine-alkylborane derivatives comprising the steps of:
reacting an amine-alkylborane compound with iodine to produce an amine-alkyliodoborane;
treating the amine-alkyliodioborane with cyanide ion to form an amine-alkylcyanoborane;
alkylating and then hydrolyzing the amine-alkylcyanoborane in order to produce an amine-(N-alkylcarbamoyl)alkylborane; and
exchanging the amine of the amine-(N-alkylcarbamoyl)alkylborane with a second amine in order to produce the final amine-(N-alkylcarbamoyl)alkylborane.

5. A process for the preparation of ammonia-(N-ethylcarbamoyl)methylborane comprising the steps of:
reacting trimethylamine-methylborane with iodine in the presence of benzene to produce trimethylamine-methyliodoborane;
treating the trimethylamine-methyliodoborane with NaCN in the presence of THF to form trimethylamine-methylcycnoborane;
alkylating the trimethylamine-methylcyanoborane with $(CH_3CH_2)_3OBF_4$ followed by hydrolysis with NaOH in order to produce trimethylamine-(N-ethylcarbamoyl)methylborane; and
reacting the trimethylamine-(N-ethylcarbamoyl) methylborane with ammonia under pressure in order to produce ammonia-(N-ethylcarbamoyl)methylborane.

6. A process for the preparation of an amine-methylborane comprising the steps of:
reacting an amine-carboxyborane of the formula $R_6BH_2COOH$ with $LiAlH_4$ in ether in order to form $LiBH_3CH_3$ wherein $R_6$ is a primary, secondary, tertiary or heterocyclic amine with the proviso that the alkyl groups of any primary, secondary or tertiary $R_6$ amine can independently or simultaneously be $C_1$-$C_{10}$ alkyl and the carbon ring of any heterocyclic $R_6$ amine can range from 4 to 10 carbon atoms; and treating the $LiBH_3CH_3$ in the presence of a hydrohalide with an amine of the formula $R_4$ wherein $R_4$ is a primary, secondary, tertiary or heterocyclic amine with the proviso that the alkyl groups of any primary, secondary or tertiary $R_4$ amine can independently or simultaneously be $C_1$-$C_{10}$ alkyl and the carbon ring of any heterocyclic $R_4$ amine can range from 4 to 10 carbon atoms and wherein $R_4$ and $R_6$ can be the same or different.

7. A process according to claim 6 wherein $R_4$ and $R_6$ are both trimethylamine and the hydrohalide is HCl.

8. A method for inducing antineoplastic activity in an animal comprising administering a therapeutic amount of an amine-alkylborane derivative.

9. A method for inducing antihyperlipidemic activity in an animal comprising administering a therapeutic amount of an amine-alkylborane derivative.

10. A method according to claim 8 or 9 wherein the amine-alkylborane derivative corresponds to the general formula:

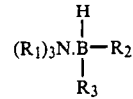

wherein $R_1$ is simultaneously or independently H, $CH_3$, or $CH_2CH_3$, with the proviso that when $(R_1)_3N$ is a primary amine, the alkyl $R_1$ can be $C_1$-$C_{10}$ linear alkyl; $R_2$ is $C_1$-$C_{10}$ alkyl or corresponds to the R group of the common amino acids; and $R_3$ is I, CN, $CNCH_2CH_3+BF_4-$ or $C(O)N(H)CH_2CH_3$.

11. A method according to claim 10 wherein $R_1$ and $R_2$ are $CH_3$ and $R_3$ is selected from the group consisting of I, CN, and $CNCH_2CH_3+BF_4-$.

12. A method according to claim 10 wherein $R_1$ is H, $R_2$ is $CH_3$ and $R_3$ is $C(O)N(H)CH_2CH_3$.

* * * * *